United States Patent [19]
Kato et al.

[11] Patent Number: 5,089,133
[45] Date of Patent: Feb. 18, 1992

[54] WATERPROOF TYPE OXYGEN SENSOR

[75] Inventors: Nobuhide Kato; Masanori Katsu, both of Aichi Pref., Japan

[73] Assignee: NGK Insulators, Ltd., Japan

[21] Appl. No.: 486,923

[22] Filed: Mar. 1, 1990

[30] Foreign Application Priority Data

Mar. 13, 1989 [JP] Japan .................................. 1-58022

[51] Int. Cl.⁵ .......................................... G01N 27/409
[52] U.S. Cl. ............................... 204/427; 204/153.18; 204/421; 204/424; 204/428
[58] Field of Search ............ 204/427, 428, 429, 153.18

[56] References Cited

U.S. PATENT DOCUMENTS

| | | | |
|---|---|---|---|
| 4,362,609 | 12/1982 | Sano et al. | 204/428 |
| 4,526,672 | 7/1985 | Reed | 204/428 |
| 4,569,748 | 2/1986 | Yamakawa et al. | 204/429 |
| 4,717,464 | 1/1988 | Oshima et al. | 204/427 |
| 4,784,743 | 11/1988 | Iino et al. | 204/425 |
| 4,786,397 | 11/1988 | Barbieri et al. | 204/427 |
| 4,786,398 | 11/1988 | Wertheimer et al. | 204/427 |
| 4,786,399 | 11/1988 | Wertheimer et al. | 204/427 |

FOREIGN PATENT DOCUMENTS

| | | | |
|---|---|---|---|
| 0215607 | 3/1987 | European Pat. Off. | 204/427 |
| 14153 | 2/1981 | Japan | 204/427 |

Primary Examiner—T. Tung
Attorney, Agent, or Firm—Parkhurst, Wendel & Rossi

[57] ABSTRACT

A waterproof type oxygen sensor including a sensor element having electrodes on inner and outer surfaces, respectively, a housing for housing the sensor element, a gas-tightly sealed section arranged inside the housing for isolating the exhaust gases from air, and a water-repelling communicating section for communicating the air inside the gas-tightly sealed section with surrounding air. The inner and outer electrodes are adapted to contact air and exhaust gases, respectively. In the oxygen sensors, $Y \geq 10X^{0.35}$ in which X and Y are a value obtained by expressing the gas-tightness of the gas-tightly sealed section as an amount of a gas passing the gas-tightly sealed section and an amount Y of a gas passing the communicating section, respectively.

3 Claims, 5 Drawing Sheets

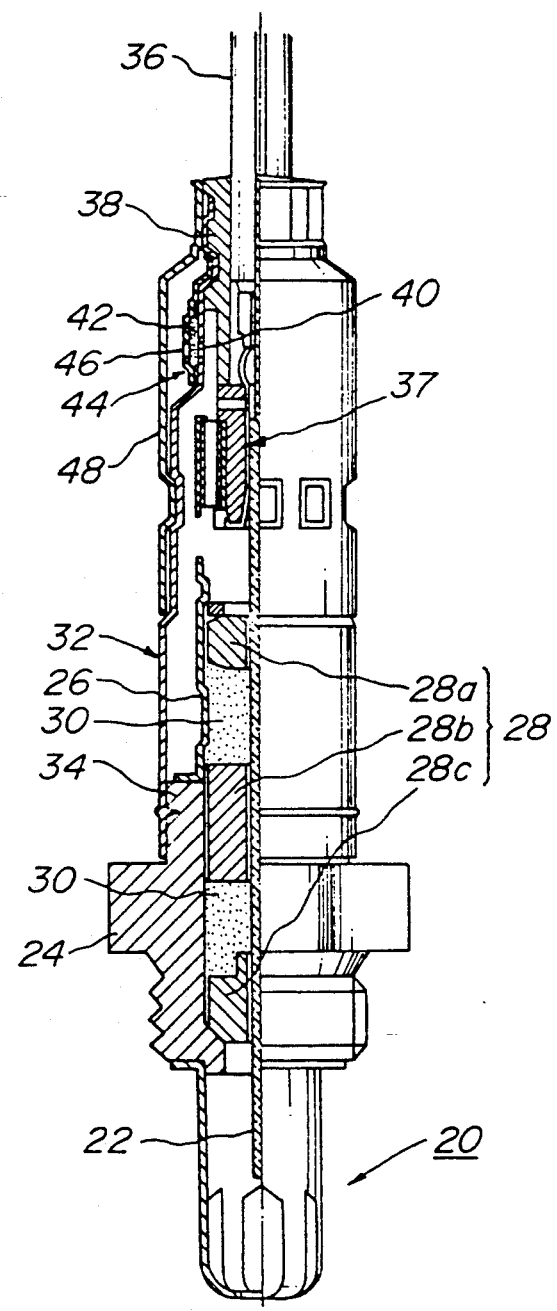
FIG_1

FIG_2a
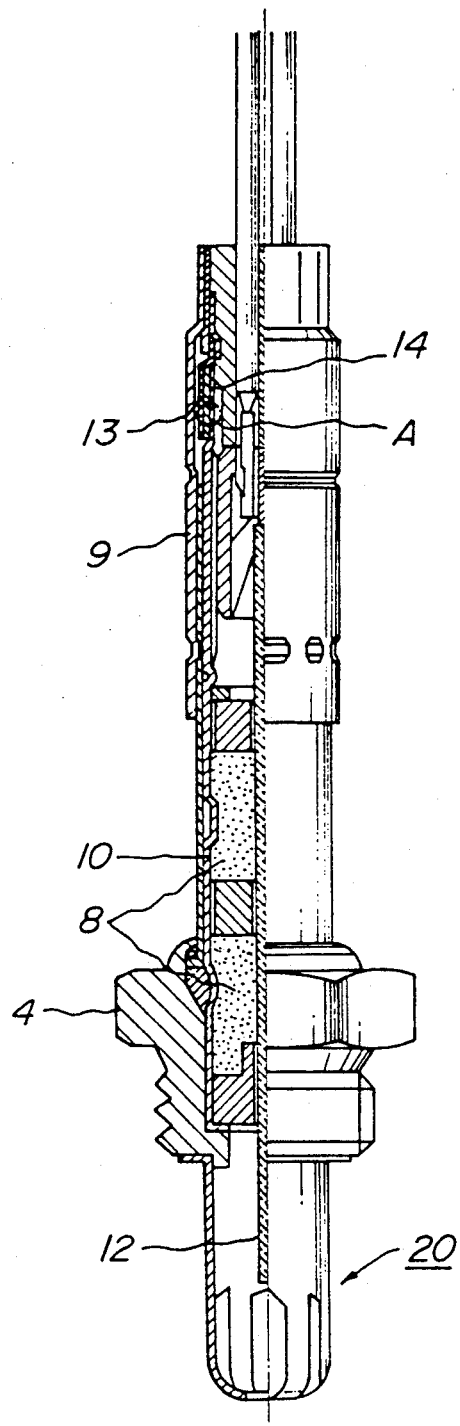
FIG_2b
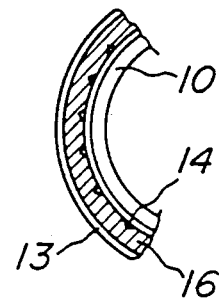

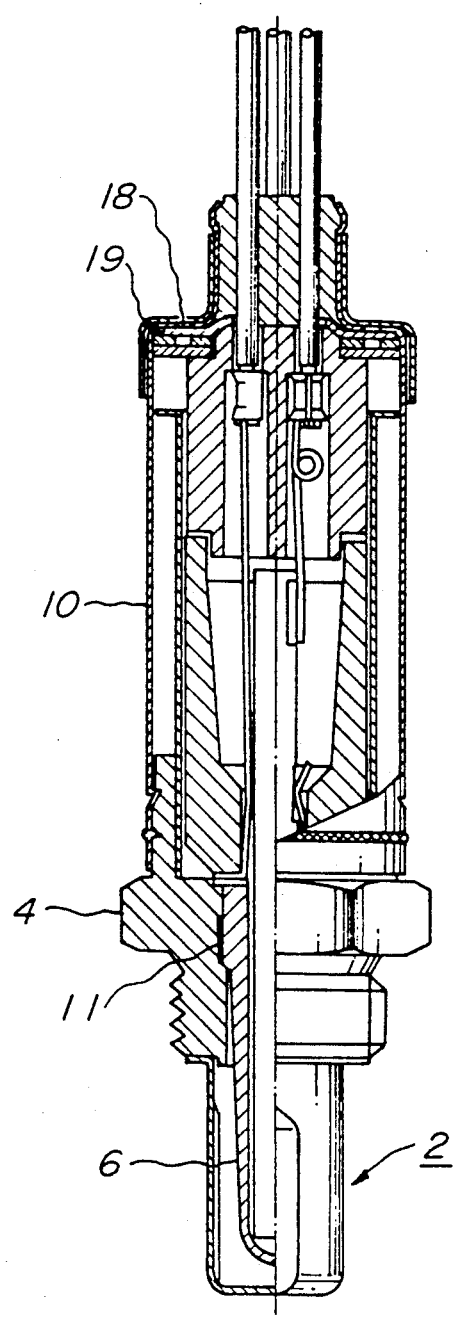
FIG_3

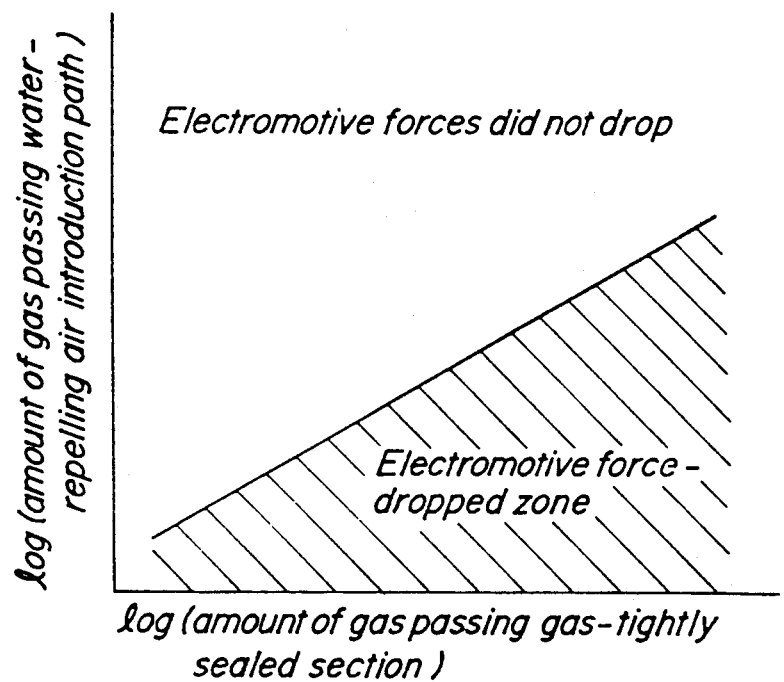
FIG_4

WATERPROOF TYPE OXYGEN SENSOR

BACKGROUND OF THE INVENTION

(1) Field of the Invention

The present invention relates to an improvement on an oxygen sensor or a so-called waterproof type oxygen sensor, comprising a sensor element having electrodes on inner and outer surfaces, respectively, which are to contact with air and exhaust gases, respectively, a housing for containing the sensor element, a gas-tightly tight sealed section provided in the housing for separating the exhaust gases from the air, and a water-repelling communicating section for communicating the air in the gas-tightly sealed section with surrounding air.

(2) Related Art Statement

Waterproof type oxygen sensors have conventionally widely been known as oxygen concentration detectors for exhaust gases in automobiles. FIGS. 2a and 2b and FIG. 3 show examples of the waterproof type oxygen sensors to which the present invention is applicable. In these figures, the same reference numerals denote the same or similar parts.

Since the oxygen sensor of this type uses air as a reference oxygen atmosphere, it is constructed to isolate air as the reference oxygen atmosphere from gases to be measured. As a way to separate air from the gas to be measured, in the case of a planar sensor element 12 as shown in FIG. 2a, a talc 8 is filled between a metallic cap 10 and a sensor element 12. In the case of an oxygen sensor as shown in FIG. 3, a metal sealing structure using a metal packing 11 is employed.

As shown, the inner electrode is separated from the gases to be measured, and an air introduction path, which rejects invasion of water is provided to introduce surrounding air into the inner electrode.

As the water-repelling air introduction path, gaps among twisted filaments of a lead wire are utilized as the air introduction path, and an opened end of the lead wire to which no water is applied is utilized as an air introduction opening. Alternatively, as shown in a cross-sectional detailed view at portion A of FIG. 2a and FIG. 2b, a ring 16 made of a water-repelling material is provided between the metallic cap 10 and a metal fixing member 13 inside a metallic boot 9, and the ring 16 is provided with small gaps 14 to repel water and pass air only. Further, as shown in FIG. 3, it is proposed that a water-repelling porous member 19 is provided at an air inlet opening 18.

However, when such oxygen sensors are used for a long time period under high load-running conditions, electromotive forces drop.

SUMMARY OF THE INVENTION

It is therefore an object of the present invention to solve the above-mentioned problems, and to provide a waterproof type oxygen sensor which causes no drops in electromotive forces under high load-running conditions even in the case of a long-term use.

The waterproof type oxygen sensor according to the present invention comprises a sensor element having electrodes on inner and outer surfaces, which electrodes are to contact with air and exhaust gases, respectively, a housing for housing the sensor element, a gas-tightly sealed section provided in the housing for isolating the exhaust gases from air, and a water-repelling communicating section for communicating air in the gas-tightly sealed section with surrounding air, and is characterized in that a value X which is obtained by expressing a gas-tightness of the gas-tightly sealed section as an amount of a gas passing therethrough and an amount Y of air passing the communicating section meet the relationship: $Y \geq 10X^{0.35}$.

The present invention is based on the discovery that in the above-mentioned construction, drops in the electromotive forces can be prevented even under high load-running conditions by specifying the relationship between the amount of the gas passing the communicating section and the gas-tightness of the gas-tightly sealed section.

That is, the present inventors examined causes for dropping the electromotive forces in conventional oxygen sensors under high load-running conditions, and found out the following facts.

(a) Since the air introduction path is constructed to have a waterproof structure, gas permeability of the air introduction path drops so that replacement of the reference air is damaged.

(b) The gas-tightness of the gas-tightly sealed section of the oxygen sensor gradually drops during use for a long time.

(c) When the oxygen sensor is continuously operated under high loads, it reaches high temperatures so that thermal expansion differs along the sensor element, such as between the metallic housing and internal parts like a cap to deteriorate the gas-tightness of the gas-tightly sealed section.

(d) The concentration of a reducing gas component, particularly, a hydrogen gas component having a good diffusing property, in the exhaust gases becomes higher during running at high loads, so that such a reducing gas component is likely to invade the inside of the oxygen sensor.

(e) When the pressure of the exhaust gas increases, the exhaust gas is likely to invade the inside of the oxygen sensor.

Therefore, it was made clear that it is important to maintain the gas-tightness of the gas-tightly sealed section and the gas permeability of the air introduction path.

For this purpose, according to the present invention, the problem of the drops in the electromotive forces is solved by appropriately setting the relationship between the gas-tightness of the gas-tightly sealed section and the gas permeability of the air introduction path.

The relationship between the gas-tightness of the gas-tightly sealed section and the gas permeability of the air introduction path is set as follows:

FIG. 4 shows the relationship among the gas-tightness of the gas-tightly sealed section (expressed by the amount of the permeated gas in FIG. 4), the amount of the gas passing the water-repelling air introduction path, and occurrence of drops in the electromotive forces. The higher the pressure of the exhaust gas and the richer the air-to-fuel ratio, the wider the electromotive force-dropped zone. The gas-tightness of the gas-tightly sealed section and the gas permeability of the water-repelling air introduction path have only to be selected to prevent the dropping of the electromotive forces even under the richest conditions and under the highest exhaust gas pressure as occurring during actual use in automobiles. Since the gas-tightness of the gas-tightly sealed section gradually decreases due to heat cyclings, vibrations, etc. during use of the automobiles, the gas-tightness and the gas permeability of the waterrepelling air introduction path are selected, expecting such decreases.

It is seen from the relationship in FIG. 4 that as the gas permeability of the water-repelling air introduction path increases and as the gas-tightness increases (in other words, as the amount of the gas passing the gas-tightly sealed section decreases), the electromotive forces are unlikely to drop. In general, since the gas permeability and the waterproof property of the water-repellent air introduction path fall in a contradictory relationship, the amount of the gas passing the water-repelling air introduction section cannot boundlessly be increased.

Since it is difficult to completely maintain the gas-tightness of the gas-tightly sealed section after use, the gas permeability of the water-repelling air introduction path is set considering the above factors based on the relationship in FIG. 4. For instance, in the case of the structure utilizing the gaps formed among the twisted filaments of the lead wire as the air introduction path, the necessary waterproof property can be maintained and the gas permeable amount can be controlled to a given level by adjusting the thickness of the lead wire and the core wire (the magnitude of the gaps can be adjusted by the thickness of the core wire). In the case of utilizing the water-repelling fine gaps as the air introduction path, the gas permeable rate is controlled by adjusting the total sectional area and the length of the fine gaps, while the water-repelling property is maintained.

In the case of the water-repelling porous member, the gas permeable amount can be determined by the porosity, the area, the thickness, etc. of the water-repelling porous material. However, if the porosity is excessively increased, the waterproof property decreases. Therefore, the necessary gas permeable rate can be assured by setting the porosity at a level satisfying the requisite for the waterproof performances, and adjusting the area and/or the thickness.

The water-repelling communicating section in the present invention means gaps formed among the twisted filaments of the lead wire, an air path separately formed from the spaces among the twisted filaments of the lead wire, fine water-repellent gaps, a water-repelling porous material or the like.

These and other objects, features and advantages of the invention will be appreciated upon reading the following description of the invention when taken in conjunction with the attached drawings, with the understanding that some variations, changes or modifications of the same could be made by the skilled person in the art to which the invention pertains without departing from the spirit of the invention or the scope of claims appended hereto.

BRIEF DESCRIPTION OF THE DRAWINGS

For a better understanding of the invention, reference is made to the attached drawings, wherein:

FIGS. 1 and 3 are partially sectional views of oxygen sensors according to the present invention;

FIGS. 2a and 2b are a partially sectional view of other oxygen sensor to which the present invention is applicable and a cross sectional detailed view of a portion A thereof, respectively;

FIG. 4 is a diagram showing the relationship among the gas-tightness of the gas-tightly sealed section, the amount of a gas passing the air introduction path, and the occurrence of the drop in electromotive forces.

DETAILED DESCRIPTION OF THE INVENTION

Figure 5:
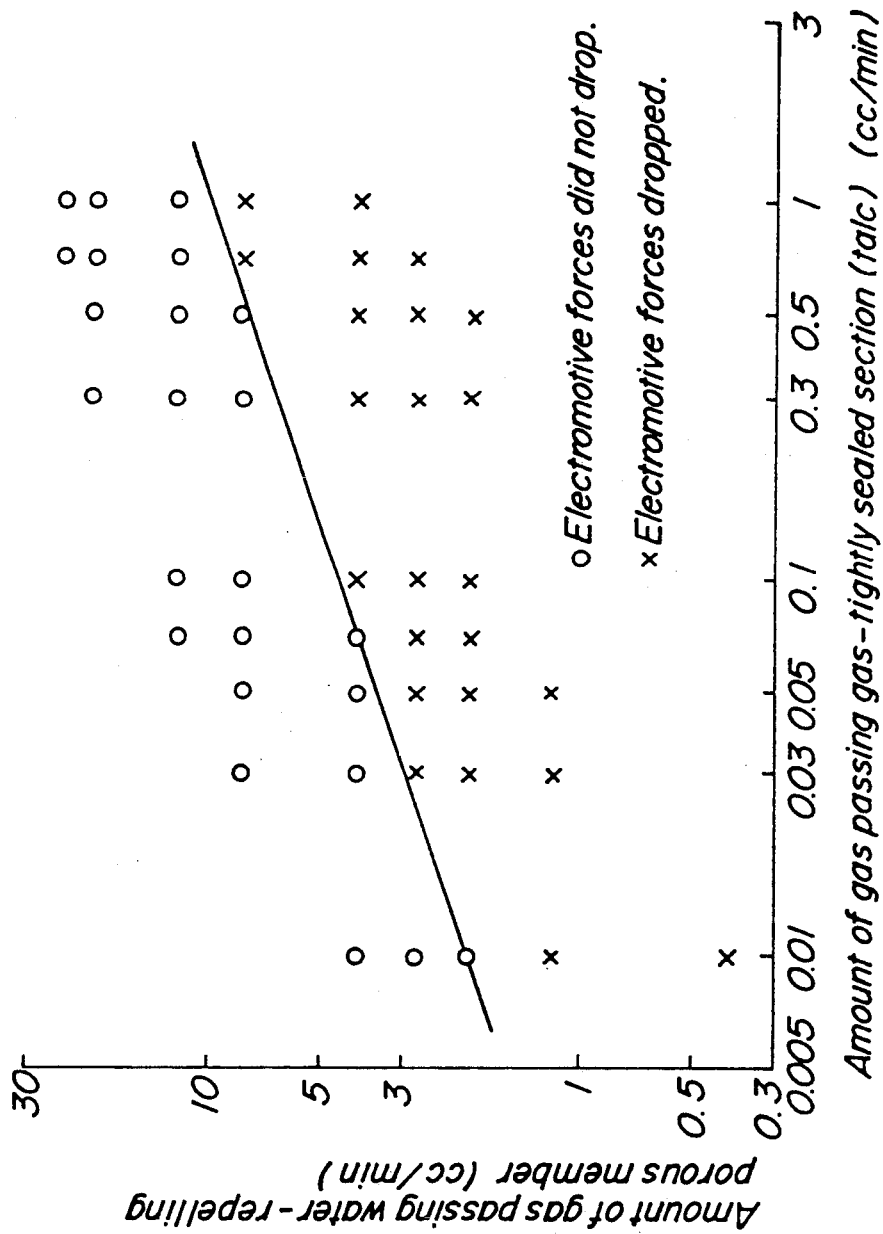
FIG. 5 is a diagram showing the relationship between the amount of the gases passing the waterrepelling porous material and the amount of the gas passing the gas-tightly sealed section in the oxygen sensor.

Specific embodiments of the present invention will be explained in detail with reference to the attached drawings.

FIG. 1 is a view illustrating an oxygen sensor to which the present invention is applied. The oxygen sensor has almost the same construction as that of known oxygen sensors. In the oxygen sensor 20 of the present invention shown in FIG. 1, a planar sensor element 22 is fixed and gas-tightly sealed relative to a metallic housing 24 and a cylindrical metallic inner tube 26 fixedly welded to the housing 24 with talc 30, which is filled among a spacer 28: 28a, 28b, 28c. In order to protect the sensor element 22 from the external environment, a metallic outer cylinder 32 is fitted around the outer periphery of an annular projection 34 of the housing 24 at an upper portion thereof. The outer cylinder is gas-tightly fixed to the entire periphery of the annular projection 34 by welding. On the other hand, the outer cylinder 32 is sealed with a rubber plug 38, which is fixed at an opening in an upper portion of the outer cylinder by caulking the plug with the outer cylinder 32, on a side opposite to a side where the outer cylinder 32 is fitted to the housing 24. A lead wire 36 is inserted through the rubber plug 38, and electrically connected to a terminal electrode 37 of the sensor element 22 at its end.

An air vent hole 40 is bored in an outer peripheral portion of the outer cylinder 32 on the side of the upper opening for assuring communication with surrounding air. A cylindrical water-repelling porous member 42 is arranged around the outer periphery of the air vent hole 40, and a cylindrical metallic fixing member 44 is fitted around the porous member 42. Upper and lower ends of the fixing metallic member 44 are caulked all around the upper and lower end portions of the porous member 42, respectively, to fix the waterrepelling porous member 42 located inside it. An air vent hole 46 is bored in a peripheral wall of the fixing member 44. Further, a metallic boot 48 is arranged to cover the fixing metallic member 44. Therefore, air passes a gap between the metallic boot 48 and the outer cylinder 32. Then, air passes through the air vent holes 46 and enters an inner space of the outer cylinder 32 through the water-repelling porous member 42 and the air vent hole 40 of the outer cylinder 32. It lastly reaches the inner electrode of the planar sensor element 22.

In the oxygen sensor constructed above, a gas-tightly sealed section is constituted by the housing 24, the inner cylinder 26, the spacer 28, the talc 30 and the sensor element 22. The gas tightness, that is, the amount of the gas passing the gas-tightly sealed section may be adjusted by varying a filling pressure of the talc. On the other hand, a communicating section is constituted by the air vent holes 40 and 46 and the water-repelling porous member 42, and the amount of the gas passing the communication section can be varied by varying the area of the air vent holes 40 and 46. While the amount of the gas passing the gas-tightly sealed section and that of the communicating section were appropriately adjusted, it was examined whether electromotive forces of the oxygen sensor dropped or not, as mentioned below.

That is, the oxygen sensor was used for 1 hour under the conditions:
(a) temperature of exhaust gases: 850–900° C.
(b) pressure of the exhaust gases: 450–500 mmHg, and
(c) air-to-fuel ratio: 9.5–10.0.

The above conditions are substantially the most severe conditions when the oxygen sensor is used, for instance, as an air-to-fuel sensor for automobiles, and further the sensor is seldom actually used continuously for one hour under such severe conditions. The reason why the case where the sensor is continuously used under constant conditions is examined is that when the conditions vary, the temperature of the exhaust gases always varies and the temperature of the oxygen sensor varies so that air inside the sensor thermally expands to cause fresh flowing of air and to exhibit no drop in the electromotive forces.

With respect to various samples of oxygen sensors, the X(cc/min) (passing amount of gas) of talc and that of a water-repelling porous member were varied, and drops in electromotive forces were measured under the above-mentioned conditions. Results are shown in Table 1.

With respect to the amount of the gas passed, the gas-tightness X (passing amount of gas) of talc was measured by using compressed air at 4 kg/cm$^2$, while the flow rate Y(cc/min) of the gas passing the water-repelling porous member was measured by using compressed air at 0.1 kg/cm$^2$. The latter amount was converted to a value at 4.0 kg/cm$^2$ to correspond to that of the talc.

TABLE 1

| Run No. | Gas-tightness of talc (flow rate of gas passed):X | Flow rate of gas passing through water-repelling porous member:Y (value calculated when pressure of compressed air would be 4.0 kg/cm$^2$) | Ratio in flow rate of gas passed Y/10X$^{0.35}$ | Drop in electromotive forces |
|---|---|---|---|---|
| 1 | 0.01 | 0.4 | 0.20 | dropped |
| 2 | 0.01 | 1.2 | 0.60 | dropped |
| 3 | 0.01 | 2.0 | 1.00 | not dropped |
| 4 | 0.01 | 2.8 | 1.40 | not dropped |
| 5 | 0.01 | 4.0 | 2.00 | not dropped |
| 6 | 0.03 | 1.2 | 0.41 | dropped |
| 7 | 0.03 | 2.0 | 0.68 | dropped |
| 8 | 0.03 | 2.8 | 0.96 | dropped |
| 9 | 0.03 | 4.0 | 1.36 | not dropped |
| 10 | 0.03 | 8.0 | 2.73 | not dropped |
| 11 | 0.05 | 1.2 | 0.34 | dropped |
| 12 | 0.05 | 2.0 | 0.57 | dropped |
| 13 | 0.05 | 2.8 | 0.80 | dropped |
| 14 | 0.05 | 4.0 | 1.14 | not dropped |
| 15 | 0.05 | 8.0 | 2.28 | not dropped |
| 16 | 0.07 | 2.0 | 0.51 | dropped |
| 17 | 0.07 | 2.8 | 0.71 | dropped |
| 18 | 0.07 | 4.0 | 1.01 | not dropped |
| 19 | 0.07 | 8.0 | 2.03 | not dropped |
| 20 | 0.07 | 12.0 | 3.04 | not dropped |
| 21 | 0.1 | 2.0 | 0.45 | dropped |
| 22 | 0.1 | 2.8 | 0.63 | dropped |
| 23 | 0.1 | 4.0 | 0.90 | dropped |
| 24 | 0.1 | 8.0 | 1.79 | not dropped |
| 25 | 0.1 | 12.0 | 2.69 | not dropped |
| 26 | 0.3 | 2.0 | 0.30 | dropped |
| 27 | 0.3 | 2.8 | 0.43 | dropped |
| 28 | 0.3 | 4.0 | 0.61 | dropped |
| 29 | 0.3 | 8.0 | 1.22 | not dropped |
| 30 | 0.3 | 12.0 | 1.83 | not dropped |
| 31 | 0.3 | 20.0 | 3.05 | not dropped |
| 32 | 0.5 | 2.0 | 0.25 | dropped |
| 33 | 0.5 | 2.8 | 0.36 | dropped |
| 34 | 0.5 | 4.0 | 0.51 | dropped |
| 35 | 0.5 | 8.0 | 1.02 | not dropped |
| 36 | 0.5 | 12.0 | 1.53 | not dropped |
| 37 | 0.5 | 20.0 | 2.55 | not dropped |
| 38 | 0.7 | 2.8 | 0.32 | dropped |
| 39 | 0.7 | 4.0 | 0.45 | dropped |
| 40 | 0.7 | 8.0 | 0.91 | dropped |
| 41 | 0.7 | 12.0 | 1.36 | not dropped |
| 42 | 0.7 | 20.0 | 2.27 | not dropped |
| 43 | 0.7 | 28.0 | 3.17 | not dropped |
| 44 | 1.0 | 4.0 | 0.4 | dropped |
| 45 | 1.0 | 8.0 | 0.8 | dropped |
| 46 | 1.0 | 12.0 | 1.2 | not dropped |
| 47 | 1.0 | 20.0 | 2.0 | not dropped |
| 48 | 1.0 | 28.0 | 2.8 | not dropped |

FIG. 5 shows a graph showing the results in Table 1. As is clear from the relationship in FIG. 5, drops in the electromotive forces during running under high loads can be prevented when the relationship between the amount Y of the gas passing the water-repelling porous member and the gas-tightness X of talc as expressed as the amount of the gas passing it meets $Y \geq 10X^{0.35}$.

The present invention is not limited to the above-mentioned examples, but various modifications, changes and variations may be made.

For instance, although the planar sensor element is used in the above examples, the invention may be applicable to oxygen sensors using sensor elements in the form of test tubes. Further, the gas-tight sealing material is not limited to talc, but cement, glass or a metal packing may be used. Furthermore, the material constituting the water-repelling communicating section is not limited to the water-repelling porous material mentioned above, but compacted glass fibers, a material obtained by coating glass fibers with a water-repelling material and compacting them, compressed graphite fibers, a material obtained by coating graphite fibers with a water-repelling material and compacting them, a material obtained by coating a material obtained by coating metallic fibers with a water-repelling material and compacting them, or a material having a gas permeability and water-repelling property may be used.

The invention may be applied to oxygen sensors each having an air introduction path which is formed with fine spaces in the water-repelling material, an air introduction path formed by utilizing gaps among twisted filaments in the lead wire, or an air introduction path formed with a space separately from the gaps among the twisted filaments inside the lead wire.

As is clear from the foregoing explanation, according to the waterproof oxygen sensor of the present invention, the electromotive forces developed when the oxygen sensor is used for a long time period under high load-running conditions can be stabilized by appropriately setting the relationship between the amount of the gas passing the communicating section and the gastightness of the gas-tightly sealed section. Thus, the durability of the oxygen sensor is improved, and the oxygen sensor is stably operated for a long time period.

What is claimed is:

1. A waterproof type oxygen sensor comprising:
   a sensor element having electrodes disposed at inner and outer portions thereof, the inner and outer electrodes being adapted to contact air and exhaust gases, respectively;
   a housing for containing the sensor element;
   a gas-tight sealed section arranged inside the housing and separating the exhaust gases from air; and
   a water-repelling section for communicating the air inside the gas-tight sealed section with surrounding air;
   wherein a relationship $Y \geq 10X^{0.35}$ between the gas-tight sealed section and the communicating section is maintained to prevent drops in electromotive forces of the oxygen sensor during operation thereof, in which X is a value (cc/min) of 0.01 to 1.0 cc/min obtained by measuring an amount of compressed air passed through the gas-tight sealed section at 4.0 kg/cm$^2$ pressure, and Y is a value (cc/min) obtained by measuring an amount of compressed air passed through the communicating section at 0.1 kg/cm$^2$ pressure, converted to a value of 4.0 kg/cm$^2$ pressure.

2. A method of producing a waterproof type oxygen sensor which is substantially unaffected by drops in electromotive forces during operation, the oxygen sensor comprising: a sensor element having electrodes disposed at inner and outer portions thereof, the inner and outer electrodes to be subjected to air and exhaust gases, respectively; a housing for containing the sensor element; a gas-tight sealed section to be arranged inside the housing for separating the exhaust gases from air; and a water-repelling section for communicating air inside said gas-tight sealed section with surrounding air; said method comprising the steps of:
   passing compressed air at 4.0 kg/cm$^2$ pressure through said gas-tight sealed section;
   passing compressed air at 0.1 kg/cm$^2$ pressure through said communicating section;
   measuring a value X (cc/min) of an amount of the air passed through said gas-tight sealed section;
   measuring a value Y (cc/min) of an amount of the air passed through said communicating section after conversion to a value at 4.0 kg/cm$^2$ pressure; and
   adjusting the gas-permeability of said communicating section such that a relationship $Y \geq 10X^{0.35}$ between said gas-tight sealed section and said communicating section is maintained.

3. The method of claim 2, wherein X ranges from 0.01 to 1.0 cc/min.

* * * * *